United States Patent
Kurochi et al.

(10) Patent No.: US 9,257,205 B2
(45) Date of Patent: Feb. 9, 2016

(54) RADIATION DETECTOR MODULE, RADIATION DETECTOR AND RADIATION IMAGING APPARATUS

(71) Applicant: General Electric Company, Schenectady, NY (US)

(72) Inventors: Haruo Kurochi, Tokyo (JP); Abdelaziz Ikhlef, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 288 days.

(21) Appl. No.: 14/091,081

(22) Filed: Nov. 26, 2013

(65) Prior Publication Data
US 2015/0146842 A1    May 28, 2015

(51) Int. Cl.
| G21F 1/00 | (2006.01) |
| G01N 23/04 | (2006.01) |
| G01T 1/29 | (2006.01) |
| G21K 1/02 | (2006.01) |

(52) U.S. Cl.
CPC .............. *G21F 1/00* (2013.01); *G01N 23/046* (2013.01); *G01T 1/2985* (2013.01); *G21K 1/025* (2013.01)

(58) Field of Classification Search
USPC ....................... 378/19, 20, 147, 149
See application file for complete search history.

(56) References Cited

U.S. PATENT DOCUMENTS

| 2004/0104350 A1* | 6/2004 | Tsuchiya | G01T 1/2928 250/370.08 |
| 2006/0165214 A1* | 7/2006 | Mattson | G01N 23/046 378/19 |
| 2007/0235654 A1 | 10/2007 | Yahata et al. | |
| 2010/0239072 A1 | 9/2010 | Kurochi | |
| 2011/0096895 A1 | 4/2011 | Kurochi | |
| 2012/0219107 A1 | 8/2012 | Kurochi et al. | |
| 2013/0163715 A1 | 6/2013 | Kurochi | |
| 2013/0223588 A1 | 8/2013 | Kurochi et al. | |
| 2013/0327947 A1* | 12/2013 | Ronda | G01T 1/1644 250/362 |

FOREIGN PATENT DOCUMENTS

| JP | 2012210291 | 11/2012 |
| JP | 2013170922 | 2/2013 |

* cited by examiner

*Primary Examiner* — Phillip A Johnston
*Assistant Examiner* — Hsien Tsai
(74) *Attorney, Agent, or Firm* — Lucas Divine; General Electric Company

(57) ABSTRACT

A detector module for a radiation detector in a radiation imaging apparatus is provided. The detector module includes a detecting element array including a plurality of detecting elements arranged in a matrix form in first and second directions orthogonal to each other, the detecting element array configured to allow radiation to penetrate through spaces defined between the detecting elements, an electronic circuit arranged on a radiation emission side of the detecting element array, and a radiation shielding body arranged on a radiation incident side of the detecting element array. The radiation shielding body includes a base material having radiation permeability and formed with a plurality of grooves extending in the first direction at respective positions corresponding to spaces between the detecting elements in the second direction, and a plurality of radiation shielding materials each inserted in a respective groove of the plurality of grooves.

20 Claims, 6 Drawing Sheets

FIG. 3A
FIG. 3B
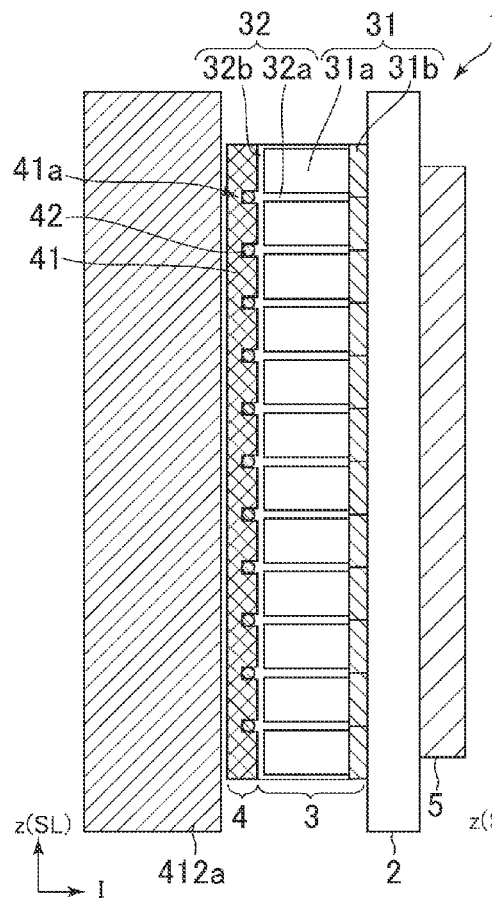
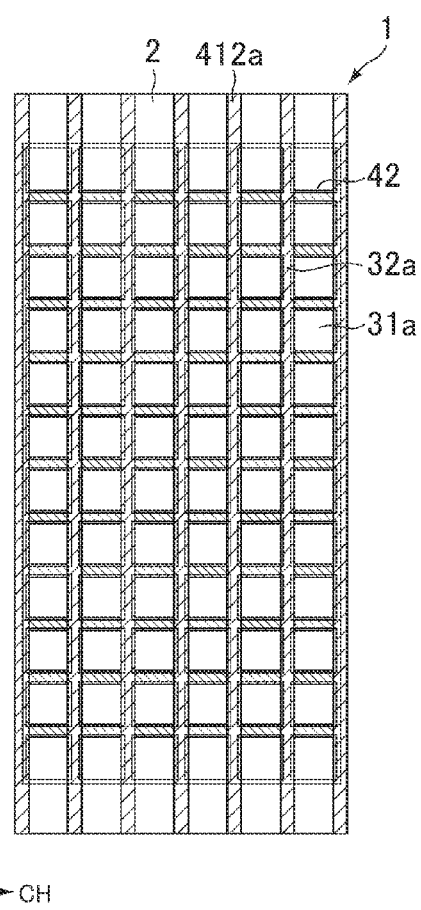
FIG. 3C
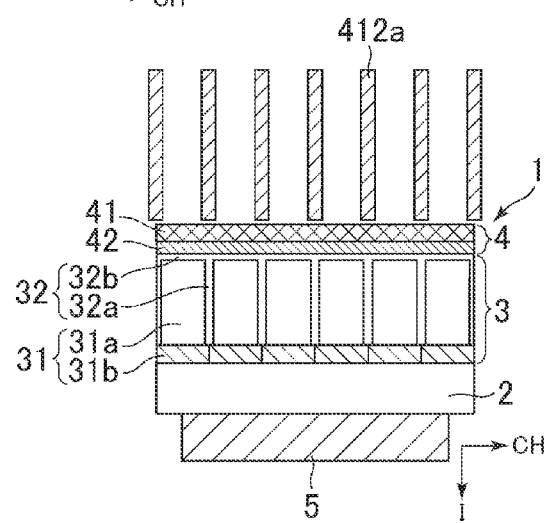

FIG. 5A
FIG. 5B
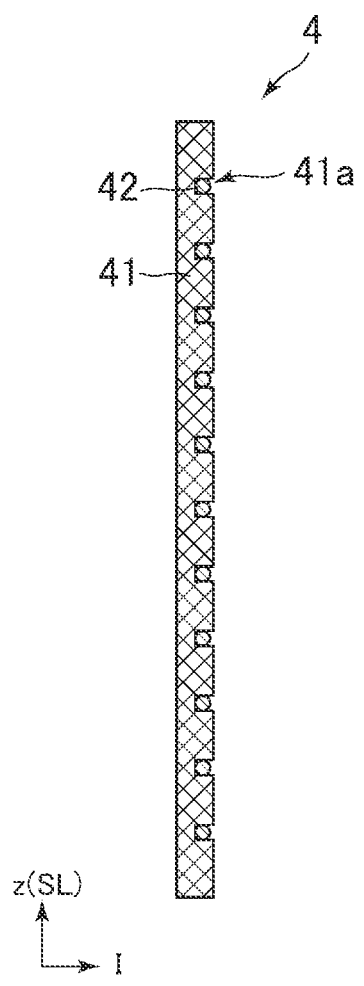
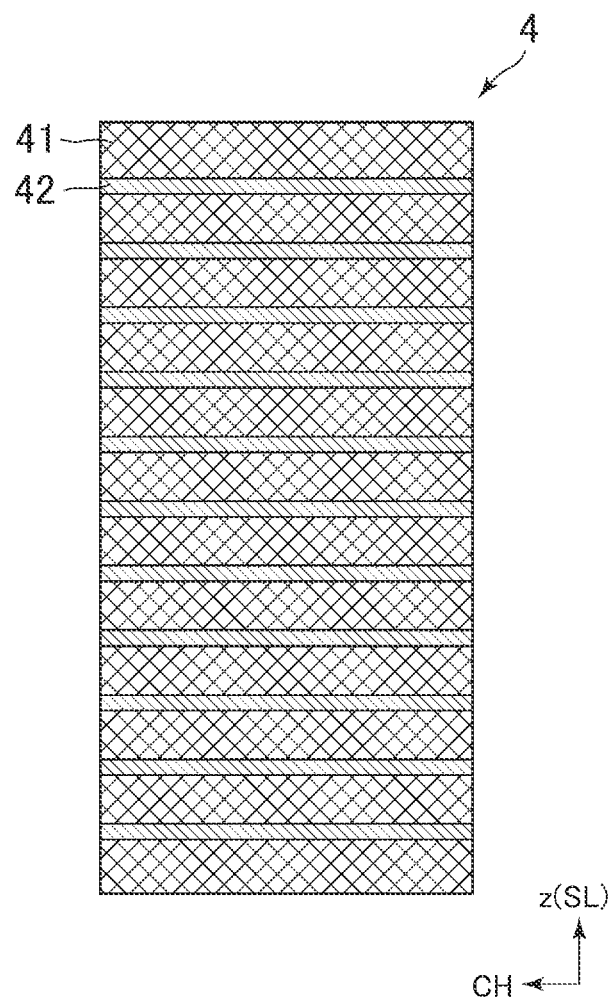

RADIATION DETECTOR MODULE, RADIATION DETECTOR AND RADIATION IMAGING APPARATUS

BACKGROUND OF THE INVENTION

The present invention relates to a technology which suppresses damage to an electronic circuit by radiation in a radiation detector module.

As a detector module that configures a radiation detector, there has been proposed one in which an electronic circuit that processes output signals of detecting elements is arranged on the back surface of a detecting element array (refer to, for example, FIG. 2 of Japanese Patent Laid-Open No. 2013-170922 and FIGS. 2 and the like of Japanese Patent Laid-Open No. 2012-210291). Such a configuration aims at shortening a connecting line between each detecting element and the electronic circuit as much as possible to thereby prevent the mixing of external noise to the output signal of the detecting element and eliminating routing of each connecting line to make a structure simple.

On the other hand, the detecting element array often includes a plurality of detecting elements arranged in a matrix form, and a wall structure formed to a lattice shape so as to divide the detecting elements respectively. Generally, if each detecting element is of a combination of a scintillator that converts incident X-rays to light and a photoelectric conversion element that converts the light to an electric signal, the wall structure becomes a reflector for reflecting light emitted from the scintillator and efficiently guiding the light on the photoelectric conversion element. The wall structure that functions as the reflector normally has X-ray permeability. The electronic circuit, particularly one including an integrated circuit such as an ASIC (Application Specific Integrated Circuit) or the like is substantially degraded in performance when irradiated with X-rays. That is, of radiation applied from a radiation tube to a detector, the radiation incident on each grid portion of the wall structure penetrates the wall structure as it is, and reaches the electronic circuit provided on the back side, thereby causing damage to the electronic circuit.

The following countermeasure has heretofore been proposed to prevent such damage. For example, there is cited a method of sticking a lattice-like radiation shielding grid including a heavy metal such as tungsten onto each grid portion of a wall structure in alignment therewith and preventing radiation from penetrating the grid portions of the wall structure.

The method using such a lattice-like radiation shielding grid is however accompanied by several problems.

For example, since the width of the radiation shielding grid often becomes very thin (e.g., about 0.2 mm), it is often fabricated by high-cost etching processing.

Further, for example, collimator plates for scattered ray removal are normally respectively disposed at positions corresponding to grid portions of a wall structure extending in a slice direction. That is, radiation does not almost arrive at the grid portions of the wall structure extending in the slice direction by a radiation shielding effect by the collimator plates. Therefore, although the grid portions extending in the slice direction at the radiation shielding grid are originally unnecessary, they are provided with another objective of mechanically supporting grid portions extending in a channel direction at the radiation shielding grid. Now consider where the width of each of the grid portions extending in the slice direction at the radiation shielding grid is temporarily not to be sufficiently smaller than the thickness of each collimator plate. In this case, mutual position errors between the collimator plates and the grid portions cause a variation in the radiation shielding effect. This will change a radiation spectrum, the intensity of scattered radiation and the like, thus causing an artifact in a reconstructed image. There is therefore a need to finish each grid portion extending in the slice direction at the radiation shielding grid more finely (e.g., less than ⅔ of the thickness of each collimator plate) by etching processing. Such processing is however very difficult technically and incurs high cost.

With the foregoing in view, there has been a demand for a detector module equipped with a detecting element array that has a plurality of detecting elements arranged in a matrix form in first and second directions orthogonal to each other and that allows radiation to penetrate through spaces defined between the detecting elements, and an electronic circuit arranged on the radiation emission side of the detecting element array. This configuration eliminates radiation shielding materials extending in the second direction while shielding against radiation in the spaces defined between the detecting elements in the second direction.

BRIEF DESCRIPTION OF THE INVENTION

In one aspect, a detector module is provided. The detector module is equipped with a detecting element array that has a plurality of detecting elements arranged in a matrix form in first and second directions orthogonal to each other and that allows radiation to penetrate through spaces defined between the detecting elements, and an electronic circuit arranged on the radiation emission side of the detecting element. The detector module further includes a radiation shielding body having a plurality of radiation shielding materials extending in the first direction, which are inserted in a base material having radiation permeability, the radiation shielding body arranged on the radiation incident side of the detecting element array. Therefore, the radiation shielding materials extending in the first direction can be supported by the base material itself, thus making it possible to eliminate other radiation shielding materials for supporting the radiation shielding materials extending in the first direction. As a result, it is possible to eliminate radiation shielding materials extending in the second direction while shielding against radiation in the spaces defined between the detecting elements in the second direction.

Further advantages will be apparent from the following description of exemplary embodiments as illustrated in the accompanying drawings.

BRIEF DESCRIPTION OF THE DRAWINGS

FIGS. 3A, 3B and 3C are diagrams depicting a configuration of a detector module;

FIGS. 5A and 5B are diagrams showing a configuration of an X-ray shielding grid plate.

DETAILED DESCRIPTION OF THE INVENTION

Exemplary embodiments will hereinafter be described. The disclosure is not limited to or by the exemplary embodiments described herein.

Figure 1:
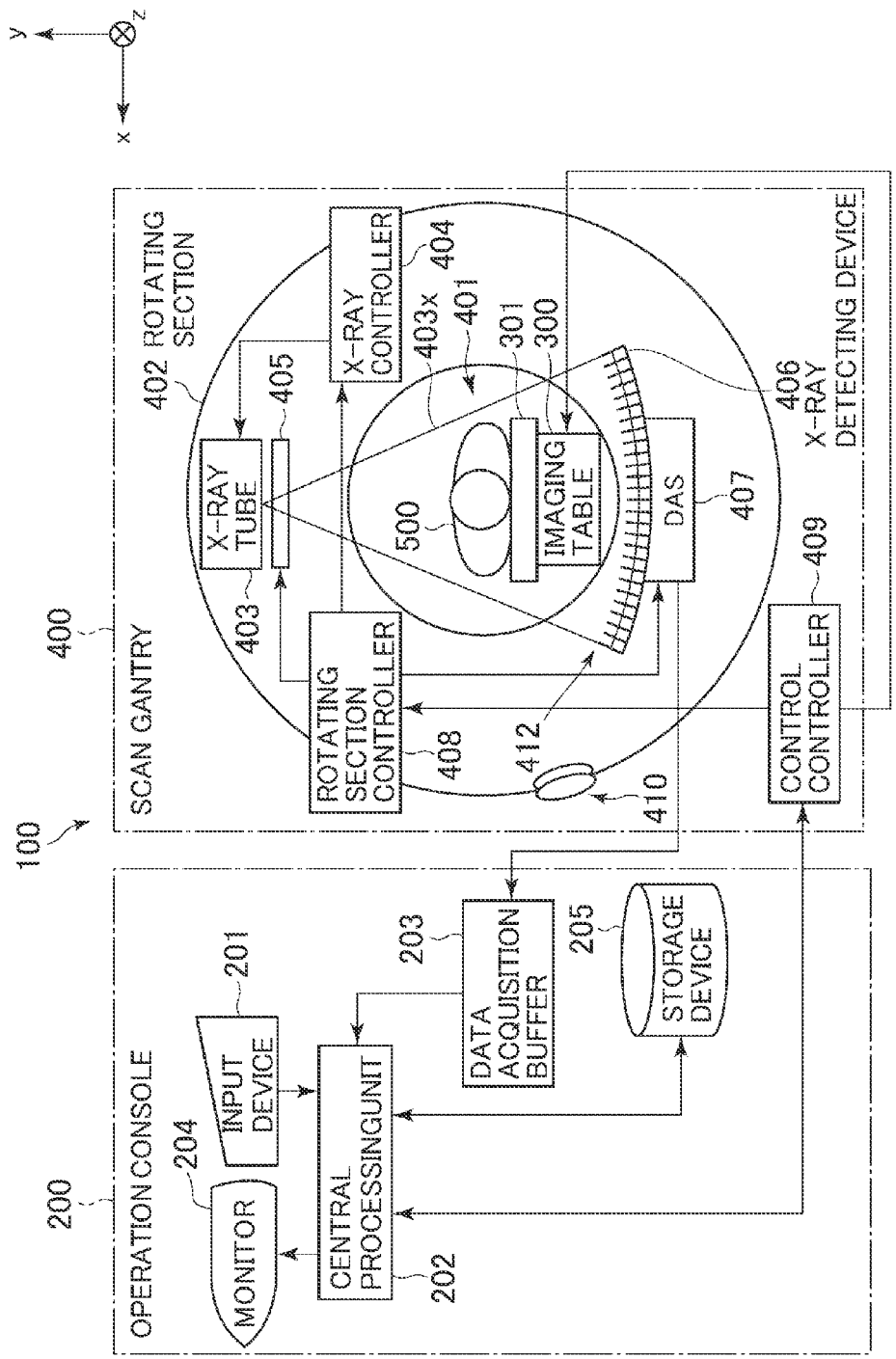
FIG. 1 is a diagram schematically showing a configuration of an X-ray CT apparatus.

FIG. 1 is a diagram schematically showing a configuration of an X-ray CT (Computed Tomography) apparatus according to an exemplary embodiment. As shown in FIG. 1, the X-ray CT apparatus 100 is equipped with an operation console 200, an imaging table 300 and a scan gantry 400.

The operation console 200 is equipped with an input device 201 which accepts an input from an operator, a central processing unit 202 which performs control of respective parts for performing imaging of a subject 500, a data process for generating an image, etc., a data acquisition buffer 203 which acquires or collects data acquired by the scan gantry 400, a monitor 204 which displays each image thereon, and a storage device 205 which stores a program, data, etc. therein.

The imaging table 300 is equipped with a cradle 301 which inserts and draws the subject 500 into and from an opening 401 of the scan gantry 400 with the subject 500 placed thereon. The cradle 301 is elevated and linearly moved horizontally by a motor built in the imaging table 300. Incidentally, in the exemplary embodiment, the direction of a body axis of the subject 500 (i.e., the horizontal linear moving direction of the cradle 301) is assumed to be a z direction, a vertical direction is assumed to be a y direction, and a horizontal direction orthogonal to the z and y directions is assumed to be an x direction.

The scan gantry 400 has an annular-shaped rotating section 402 which is rotatably supported about the opening 401. The rotating section 402 is provided with an X-ray tube 403, an X-ray controller 404 which controls the X-ray tube 403, an aperture 405 which shapes X-rays 403x generated from the X-ray tube 403 into a fan beam or a cone beam, an X-ray detecting device 406 which detects the X-rays 403x penetrated through the subject 500, a DAS (Data Acquisition System) 407 which converts the outputs of the X-ray detecting device 406 into X-ray projection data and acquires or collects the same, and a rotating section controller 408 which controls the X-ray controller 404, aperture 405, X-ray detecting device 406 and DAS 407. The scan gantry 400 is equipped with a control controller 409 which performs communication of control signals or the like with the operation console 200 and the imaging table 300. The rotating section 402 is electrically connected to a portion supporting it via a slip ring 410.

The X-ray tube 403 and the X-ray detecting device 406 are disposed opposite to each other with an imaging space in which the subject 500 is placed (i.e., the opening 401 of the scan gantry 400) interposed therebetween. When the rotating section 402 is rotated, the X-ray tube 403 and the X-ray detecting device 406 are rotated about the subject 500 while their positional relation with one another is maintained. The X-rays 403x shown in the form of the fan beam or cone beam, which are radiated from the X-ray tube 403 and shaped by the aperture 405, penetrate the subject 500 and are applied onto a detection surface of the X-ray detecting device 406. The direction of expansion of the X-rays 403x shown in the form of this fan beam or cone beam at an xy plane is called a channel direction (CH direction), and the direction of expansion thereof in the z direction or the z direction itself is called a slice direction (SL direction). The direction in which X-rays are radiated from the X-ray tube 403 is called an X-ray irradiation direction (I direction). Incidentally, the channel direction and the slice direction are respectively one example illustrative of first and second directions.

The configuration of the X-ray detecting device 406 will now be described in detail.

Figure 2A:
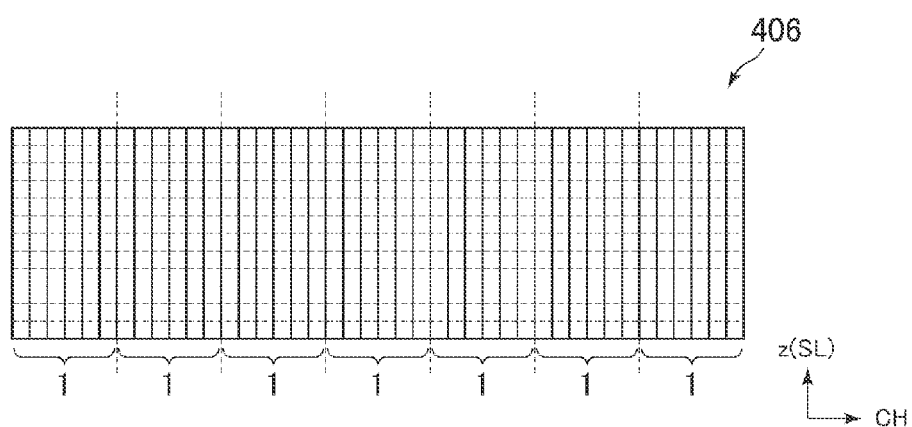
FIGS. 2A and 2B are diagrams illustrating a configuration example of an X-ray detecting device.
Figure 2B:
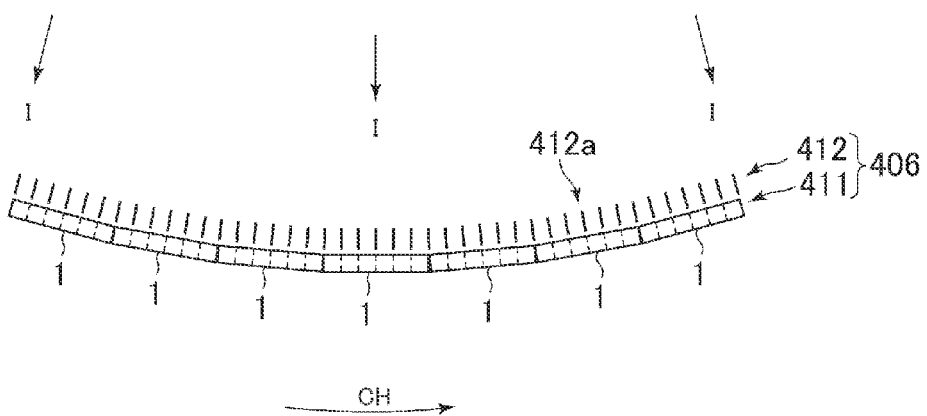

FIGS. 2A and 2B are diagrams showing the configuration of the X-ray detecting device 406. FIG. 2A is a diagram (front diagram) as the X-ray detecting device 406 is viewed in the I direction, and FIG. 2B is a diagram (side diagram) as the X-ray detecting device 406 is viewed in the SL direction.

As shown in FIGS. 2A and 2B, the X-ray detecting device 406 is equipped with an X-ray detector 411 and a collimator device 412. The X-ray detector 411 has a plurality of detector modules 1 arranged side by side in the CH direction. The collimator device 412 is disposed on the X-ray incident side of the X-ray detector 411. The collimator device 412 has a plurality of collimator plates 412a arranged at prescribed intervals in the CH direction.

FIGS. 3A, 3B and 3C are diagrams showing the configuration of the detector module 1. FIG. 3A is a diagram as the detector module 1 is viewed in the CH direction, FIG. 3B is a diagram as the detector module I is viewed in the I direction, and FIG. 3C is a diagram as the detector module I is viewed in the SL direction. Incidentally, FIGS. 3A, 3B, and 3C represent part of the detector module 1 in translucent form to easily understand the configuration thereof.

As shown in FIGS. 3A, 3B and 3C, the detector module 1 has a module substrate 2, a detecting element array 3, an X-ray shielding grid plate 4 and an electronic circuit 5. Incidentally, the X-ray shielding grid plate 4 is one example illustrative of a radiation shielding body.

The module substrate 2 has a plate shape including an approximately rectangular plate surface and includes ceramic or the like.

The detecting element array 3 is disposed on the X-ray incident side of the module substrate 2.

Figure 4A:
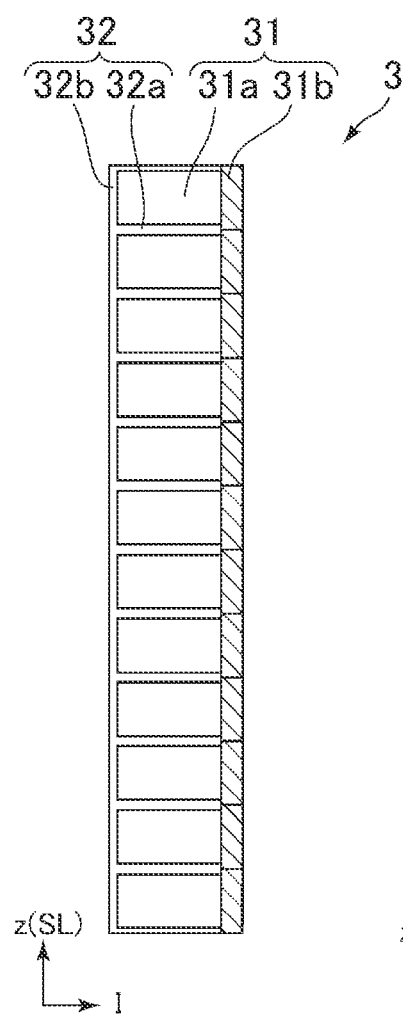
FIGS. 4A and 4B are diagrams showing a configuration of a detection element array.
Figure 4B:
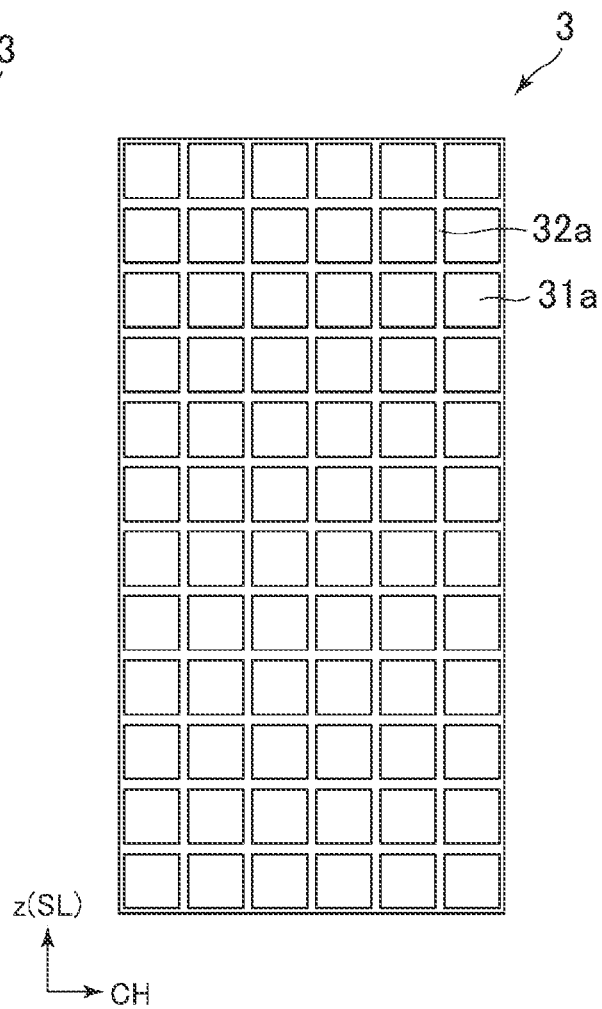

FIGS. 4A and 4B are diagrams showing the configuration of the detecting element array 3. FIG. 4A is a diagram as the detecting element array 3 is seen in the CH direction, and FIG. 4B is a diagram as the detecting element array 3 is viewed in the I direction.

As shown in FIGS. 3A, 3B, 3C, 4A and 4B, the detecting element array 3 includes a plurality of detecting elements 31 and a wall structure 32. Incidentally, the wall structure 32 is one example illustrative of a light-reflecting member.

The detecting elements 31 are arranged in a matrix form in the CH and SL directions. For example, detecting elements 31 in a grid of 64 (CH direction)×128 (SL direction) are arranged for each detector module 1 in the exemplary embodiment.

An X-ray incident surface of each detecting element 31 has an approximately square shape whose one side is about 1.0 millimeters (mm) in width. Incidentally, for convenience, the number of detecting elements 31 shown in FIGS. 3A, 3B, 3C, 4A and 4B in less than the actual number.

The detecting element 31 includes a configuration in which a scintillator 31a that converts an incident X-ray into light, and a photoelectric conversion element 31b that converts light emitted from the scintillator 31a into an electric signal are overlaid together in the I direction. The photoelectric conversion element 31b includes a photo-diode, for example.

The wall structure 32 includes wall portions 32a extending in a grid shape in the CH and SL directions so as to divide the detecting elements 31 respectively, and a lid portion 32b that covers the detecting elements 31 from the X-ray incident side. That is, the wall portions 32a are respectively placed in spaces between the respective adjacent detecting elements 31 in the detecting elements 31 arranged in a matrix form. The wall structure 32 has light (visible light) reflectivity and X-ray permeability. The wall structure 32 functions as a reflector which reflects light emitted from each scintillator 31a and allows it to enter into the photoelectric conversion element 31b. The wall thickness of the wall structure 32 is equivalent to the width of the space defined between the detecting elements 31 and is about 0.1 mm in the exemplary embodiment.

The X-ray shielding grid plate 4 is arranged on the X-ray incident surface of the detecting element array 3.

FIGS. 5A and 5B are diagrams showing the configuration of the X-ray shielding grid plate 4. FIG. 5A is a diagram as the X-ray shielding grid plate 4 is viewed in the CH direction, and FIG. 5B is a diagram as the X-ray shielding grid plate 4 is viewed in the I direction.

As shown in FIGS. 3A, 3B, 3C, 5A and 5B, the X-ray shielding grid plate 4 has a base material 41 and a plurality of X-ray shielding materials 42.

The base material 41 is shaped in a plate-like fashion. The thickness of the base material 41 is 0.4 mm or larger and 1.0 mm or smaller, for example. In the exemplary embodiment, the thickness thickness of the base material 41 is 0.5 mm. The base material 41 is formed with a plurality of grooves 41a that extend in the CH direction at respective positions corresponding to the spaces defined between the detecting elements 31 as viewed in the SL direction. The SL-direction width of each groove 41a is 0.3 mm, for example. The base material 41 has X-ray permeability. The base material 41 includes, for example, a carbon resin such as CFRP (carbon-fiber-reinforced plastic) or the like.

The X-ray shielding materials 42 are respectively inserted into the grooves 41a in the base material 41 and adhesively fixed thereto. The X-ray shielding materials 42 respectively have X-ray shielding properties, i.e., strong X-ray absorbing properties. The X-ray shielding materials 42 respectively include, for example, a heavy metal such as tungsten, molybdenum or the like. Each of the X-ray shielding materials 42 is one in which a heavy metal is formed in a wire or bar form or one in which powder of a heavy metal is fixed and molded in a slender form. The width in the SL direction, of each of the X-ray shielding materials 42 is, for example, a width equivalent to the length more than or equal to the width of the space between the detecting elements 31 (equal to the wall thickness of the wall structure 32) and less than or equal to three times that width. When the wall thickness of the wall structure 32 is 0.12 mm, the SL-direction width of the X-ray shielding material 42 is 0.3 mm, for example.

The electronic circuit 5 is arranged on the X-ray emission side of the module substrate 2. The electronic circuit 5 includes a circuit which processes a signal outputted from each of the detecting elements 31. The electronic circuit 5 includes, for example, an integrated circuit such as an ASIC or the like.

As shown in FIGS. 3A, 3B, and 3C, the collimator plates 412a are provided so as to divide the detecting elements 31 of the X-ray detector 411 in the CH direction. Also, each of the collimator plates 412a is provided in such a manner that its plate surface becomes parallel with an X-ray irradiation direction as viewed from an X-ray focal point 403f. The width in an X-ray irradiation direction (i.e., I direction) of each collimator plate 412a is 20 mm, for example. The thickness of the collimator plate 412a is 0.2 mm, for example.

Figure 6:
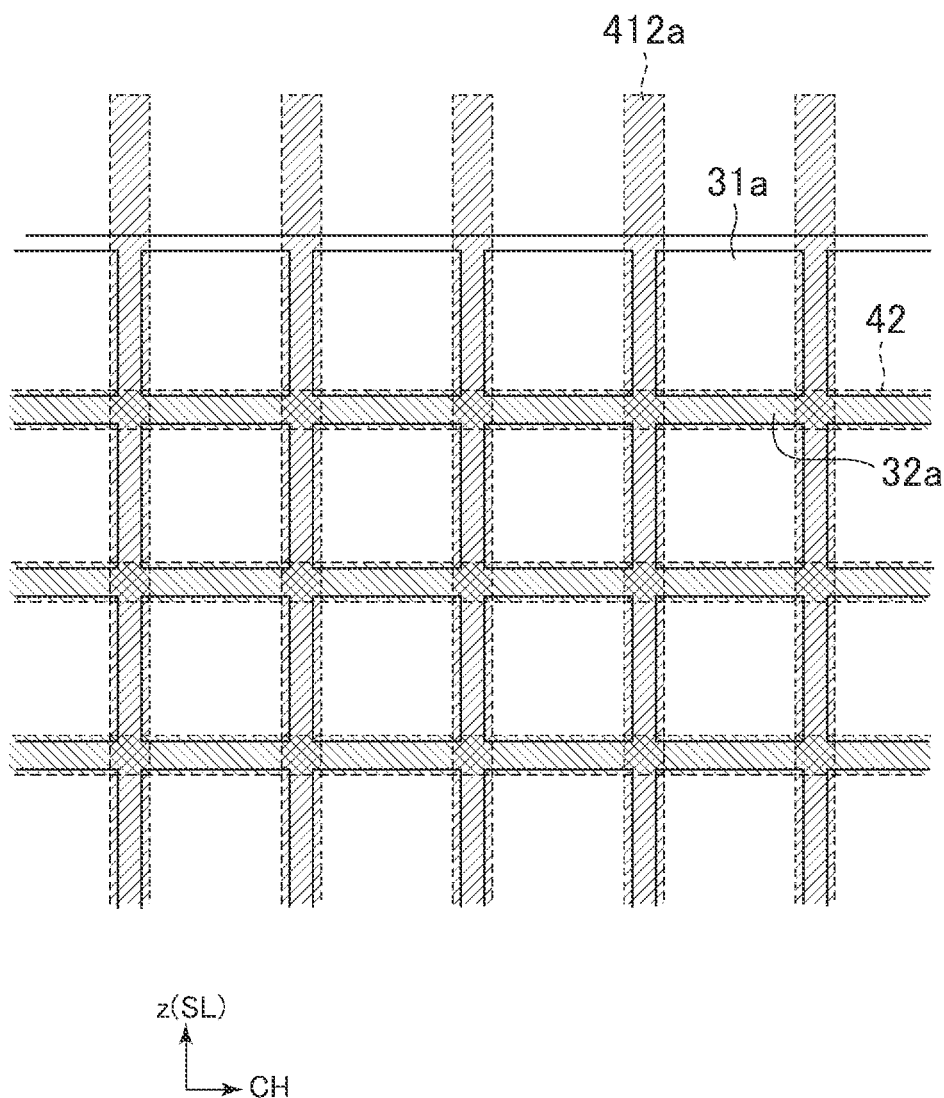
FIG. 6 is a diagram illustrating a mutual positional relationship between a wall structure, collimator plates and X-ray shielding materials.

FIG. 6 is a diagram showing a mutual positional relationship between the wall structure 32, the collimator plates 412a and the X-ray shielding materials 42. In the X-ray detecting device 406 configured in this manner, as shown in FIG. 6, the portions extending parallel with the CH direction, of the grid-like wall portions 32a of the wall structure 32 in the detecting element array 3 are shielded against X-rays by the X-ray shielding materials 42, and the portions thereof extending parallel with the SL direction are shielded against the X-rays by the collimator plates 412a. It is thus possible to selectively shield the X-rays trying to enter the grid-like wall portions 32a of the wall structure 32 in the detecting element array 3 and prevent damage to the electronic circuit 5 by the X-rays that penetrate through and arrive at the grid-like wall portions 32a of the wall structure 32.

According to the exemplary embodiment, the shielding grid plate 4 having embedded the X-ray shielding materials 42 extending in the CH direction in the base material 41 having the X-ray permeability is directly stuck onto the detecting element array 3. Therefore, the X-ray shielding materials extending in the SL direction for supporting the X-ray shielding materials 42 extending in the CH direction may not be necessary. It is therefore possible to suppress an adverse effect on the image quality of a reconstructed image, which is caused by the existence of the extra X-ray shielding materials for the purpose of the corresponding support. Since there is adopted the system of embedding the X-ray shielding materials in the grooves 41a of the base material 41 in advance, it is possible to process the grooves 41a at high accuracy and precisely perform a position alignment between the wall structure 32 and each X-ray shielding material 42 extending in the CH direction, thus making it possible to effectively prevent damage to the electronic circuit 5 by the X-rays.

Further, since it is possible to lift up the X-ray shielding grid plate 4 embedded with the X-ray shielding materials 42 extending in the CH direction by a suction cup upon assembly of the detector module 1, a Pick-and-Place type vision positioning automatic bonding device can be used. It is therefore possible to accurately capture the positions of the X-ray shielding materials 42 embedded in the X-ray shielding grid plate 4 and the positions of the grids of the wall structure 32, align them with each other with high accuracy and apply the X-ray shielding grid plate 4 onto the detecting element array 3.

Furthermore, it is possible to hold down the production cost by resin-molding the X-ray shielding grid plate 4 embedded with the X-ray shielding materials 42 in mass production.

Incidentally, the disclosure is not limited to the above exemplary embodiment and can be changed in various ways within the spirit and scope of the invention.

For example, although the exemplary embodiment is implemented using an X-ray CT apparatus, the disclosure is widely applicable to the whole radiation imaging apparatus.

Further, for example, the systems and methods described herein can be applied even to a PET-CT apparatus or SPECT-CT apparatus in which the X-ray CT apparatus and PET (Polyethylene Terephthalate) or SPECT (Single Photon Emission Computed Tomography) are combined together, etc.

What is claimed is:

1. A detector module for a radiation detector in a radiation imaging apparatus, the detector module comprising:
   a detecting element array comprising a plurality of detecting elements arranged in a matrix form in first and second directions orthogonal to each other, the detecting element array configured to allow radiation to penetrate through spaces defined between the detecting elements;
   an electronic circuit arranged on a radiation emission side of the detecting element array; and
   a radiation shielding body arranged on a radiation incident side of the detecting element array, the radiation shielding body comprising:
      a base material having radiation permeability and formed with a plurality of grooves extending in the first direction at respective positions corresponding to spaces between the detecting elements in the second direction; and
      a plurality of radiation shielding materials each inserted in a respective groove of the plurality of grooves.

2. The detector module according to claim 1, wherein the base material includes a carbon resin.

3. The detector module according to claim 1, wherein the base material is formed in a plate-like fashion.

4. The detector module according to claim 3, wherein the base material has a plate thickness greater than or equal to 0.2 mm and less than or equal to 1 mm.

5. The detector module according to claim 1, wherein the radiation shielding materials each contain one of tungsten and molybdenum.

6. The detector module according to claim 1, wherein the radiation shielding materials are each molded in a wire form, in a bar form, or by hardening powder.

7. The detector module according to claim 1, wherein the radiation shielding materials each have a width in the second direction that is equivalent to a length that is from one to three times a width of each of the spaces.

8. The detector module according to claim 1, wherein the detecting elements each comprise a scintillator and a photoelectric conversion element.

9. The detector module according to claim 1, wherein the detecting element array comprises a light-reflecting member positioned in the spaces.

10. The detector module according to claim 1, wherein the electronic circuit comprises a circuit configured to process signals outputted from the detecting elements.

11. The detector module according to claim 1, wherein the electronic circuit comprises an integrated circuit.

12. A radiation detecting device comprising:
a radiation detector in which a plurality of detector modules according to claim 1 are arranged in the first direction; and
a plurality of collimator plates arranged on a radiation incident side of the radiation detector and each extending in the second direction at respective positions corresponding to the spaces defined between the detecting elements in the first direction.

13. A radiation detecting device comprising:
a radiation detector in which a plurality of detector modules according to claim 2 are arranged in the first direction; and
a plurality of collimator plates arranged on a radiation incident side of the radiation detector and each extending in the second direction at respective positions corresponding to the spaces defined between the detecting elements in the first direction.

14. A radiation detecting device comprising:
a radiation detector in which a plurality of detector modules according to claim 11 are arranged in the first direction; and
a plurality of collimator plates arranged on a radiation incident side of the radiation detector and each extending in the second direction at respective positions corresponding to the spaces defined between the detecting elements in the first direction.

15. A radiation imaging apparatus comprising a radiation detecting device according to claim 12.

16. A radiation imaging apparatus comprising a radiation detecting device according to claim 13.

17. A radiation imaging apparatus comprising a radiation detecting device according to claim 14.

18. The radiation imaging apparatus according to claim 15, wherein the radiation imaging apparatus is configured to perform radiation tomographic imaging.

19. The radiation imaging apparatus according to claim 16, wherein the radiation imaging apparatus is configured to perform radiation tomographic imaging.

20. The radiation imaging apparatus according to claim 17, wherein the radiation imaging apparatus is configured to perform radiation tomographic imaging.

* * * * *